(12) United States Patent
Yanagawa et al.

(10) Patent No.: US 9,815,047 B2
(45) Date of Patent: Nov. 14, 2017

(54) CATALYST FOR PRODUCING MONOCYCLIC AROMATIC HYDROCARBON AND PRODUCTION METHOD OF MONOCYCLIC AROMATIC HYDROCARBON

(75) Inventors: Shinichiro Yanagawa, Tokyo (JP); Masahide Kobayashi, Tokyo (JP); Yasuyuki Iwasa, Tokyo (JP); Ryoji Ida, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 590 days.

(21) Appl. No.: 13/976,655

(22) PCT Filed: Dec. 28, 2011

(86) PCT No.: PCT/JP2011/080390
§ 371 (c)(1),
(2), (4) Date: Jun. 27, 2013

(87) PCT Pub. No.: WO2012/091092
PCT Pub. Date: Jul. 5, 2012

(65) Prior Publication Data
US 2013/0289325 A1  Oct. 31, 2013

(30) Foreign Application Priority Data
Dec. 28, 2010  (JP) ................................. 2010-294185

(51) Int. Cl.
| | | |
|---|---|---|
| C07C 4/06 | (2006.01) |
| B01J 29/70 | (2006.01) |
| C10G 11/18 | (2006.01) |
| C10G 47/16 | (2006.01) |
| C10G 11/05 | (2006.01) |
| B01J 29/85 | (2006.01) |
| B01J 37/00 | (2006.01) |
| C01B 39/48 | (2006.01) |
| C01B 39/10 | (2006.01) |

(52) U.S. Cl.
CPC .............. *B01J 29/70* (2013.01); *B01J 29/85* (2013.01); *B01J 37/0009* (2013.01); *B01J 37/0036* (2013.01); *C01B 39/10* (2013.01); *C01B 39/48* (2013.01); *C07C 4/06* (2013.01); *C10G 11/05* (2013.01); *C10G 11/18* (2013.01); *C10G 47/16* (2013.01); *B01J 2229/186* (2013.01); *C07C 2529/06* (2013.01); *C07C 2529/40* (2013.01); *C10G 2300/107* (2013.01); *C10G 2300/1033* (2013.01); *C10G 2300/1048* (2013.01); *C10G 2300/1051* (2013.01); *C10G 2300/1055* (2013.01); *C10G 2300/1059* (2013.01); *C10G 2300/301* (2013.01); *C10G 2400/30* (2013.01)

(58) Field of Classification Search
USPC ........................................................ 585/476
See application file for complete search history.

(56) References Cited

U.S. PATENT DOCUMENTS

2008/0293561 A1* 11/2008 Long ....................... B01J 29/06
502/65

FOREIGN PATENT DOCUMENTS

| | | |
|---|---|---|
| CN | 1391500 A | 1/2003 |
| CN | 1694844 A | 11/2005 |
| EP | 1762299 A1 | 3/2007 |
| JP | H03-002128 A | 1/1991 |
| JP | H03-026791 A | 2/1991 |
| JP | H03-052993 A | 3/1991 |
| JP | H11-035496 A | 2/1999 |
| JP | 2002-525380 A | 8/2002 |
| JP | 2007-137840 A | 6/2007 |
| JP | 2007-190520 A | 8/2007 |
| JP | 2007-530266 A | 11/2007 |
| WO | 0018853 A1 | 4/2000 |
| WO | 2004039725 A2 | 5/2004 |
| WO | 2010109897 A1 | 9/2010 |

OTHER PUBLICATIONS

Notice of Allowance dated Aug. 18, 2015 in JP App No. 2014-239361.
Int'l Search Report dated Mar. 6, 2012 in Int'l Application No. PCT/JP2011/080390.
Xie et al, "Porous catalytic materials of new structure and high performance," China Petrochemical Press Co. Ltd, Beijing, China, pp. 244-253 (Jan. 31, 2010).
Song et al, "Phosphorus-modified ZSM-5 for conversion of ethanol to propylene," Applied Catalysis A: General, vol. 384, pp. 201-205 (2010).
Extended European Search Report dated Aug. 13, 2014 in EP Application No. 11853109.4.
Office Action dated Jun. 13, 2014 in CN Application No. 201180062850.9.

* cited by examiner

*Primary Examiner* — Elizabeth Wood
(74) *Attorney, Agent, or Firm* — Panitch Schwarze Belisario & Nadel LLP

(57) ABSTRACT

The catalyst for producing aromatic hydrocarbon is for producing monocyclic aromatic hydrocarbon having 6 to 8 carbon number from oil feedstock having a 10 volume % distillation temperature of 140° C. or higher and a 90 volume % distillation temperature of 380° C. or lower and contains crystalline aluminosilicate and phosphorus. A molar ratio (P/Al ratio) between phosphorus contained in the crystalline aluminosilicate and aluminum of the crystalline aluminosilicate is from 0.1 to 1.0. The production method of monocyclic aromatic hydrocarbon is a method of bringing oil feedstock having a 10 volume % distillation temperature of 140° C. or higher and a 90 volume % distillation temperature of 380° C. or lower into contact with the catalyst for producing monocyclic aromatic hydrocarbon.

9 Claims, No Drawings

CATALYST FOR PRODUCING MONOCYCLIC AROMATIC HYDROCARBON AND PRODUCTION METHOD OF MONOCYCLIC AROMATIC HYDROCARBON

CROSS-REFERENCE TO RELATED APPLICATION

This application is a Section 371 of International Application No. PCT/JP2011/080390, filed Dec. 28, 2011, which was published in the Japanese language on Jul. 5, 2012 under International Publication No. WO 2012/091092 A1, and the disclosure of which is incorporated herein by reference.

TECHNICAL FIELD

The present invention relates to a catalyst for producing monocyclic aromatic hydrocarbon that is for producing monocyclic aromatic hydrocarbon from oil containing a large amount of polycyclic aromatic hydrocarbon and a production method of monocyclic aromatic hydrocarbon.

Priority is claimed on Japanese Patent Application No. 2010-294185, filed Dec. 28, 2010, the content of which is incorporated herein by reference.

BACKGROUND ART

Light Cycle Oil (hereinafter, called "LCO") as cracked light oil that is generated by a fluidized catalytic cracking contains a large amount of polycyclic aromatic hydrocarbon and is used as light oil or heavy oil. However, in recent years, investigations have been conducted to obtain, from LCO, monocyclic aromatic hydrocarbons having 6 to 8 carbon numbers (for example, benzene, toluene, xylene, ethylbenzene and the like), which can be utilized as high octane value gasoline base materials or petrochemical feedstocks and have a high added value.

For example, Patent Documents 1 to 3 suggest methods for producing monocyclic aromatic hydrocarbons from polycyclic aromatic hydrocarbons that are contained in LCO and the like in a large amount, by using a zeolite catalyst.

However, Patent Documents 1 to 3 do not disclose that the yield of monocyclic aromatic hydrocarbon having 6 to 8 carbon number produced by the method is sufficiently high.

When monocyclic aromatic hydrocarbon is produced from heavy crude oil containing polycyclic aromatic hydrocarbon, catalyst regeneration for removing a carbonaceous substance needs to be performed with a high frequency since a large amount of carbonaceous substance is precipitated on the catalyst and rapidly decreases the activity. Moreover, when a circulating fluidized bed for performing a process of efficiently repeating reaction-catalyst regeneration is employed, the temperature for catalyst regeneration needs to be higher than the reaction temperature, so the temperature environment of the catalyst becomes more severe.

When a zeolite catalyst is used as a catalyst under such a severe condition, hydrothermal deterioration of the catalyst continues, and the reaction activity decreases over time. Accordingly, the improvement of hydrothermal stability is required for the catalyst. However, for the zeolite catalyst disclosed in Patent Documents 1 to 3, a measure for improving hydrothermal stability was not taken, and the practical usefulness thereof was extremely low.

As the method for improving hydrothermal stability, a method using zeolite having a high Si/Al ratio, a method of stabilizing a catalyst by performing hydrothermal treatment in advance, such as USY-type zeolite, a method of adding phosphorus to zeolite, a method of adding a rare-earth metal to zeolite, a method of improving a structure directing agent at the time of zeolite synthesis, and the like are known.

Among these, addition of phosphorus is known to have effects that improve not only the hydrothermal stability but also the selectivity resulting from inhibiting the precipitation of a carbonaceous substance during fluidized catalytic cracking, abrasion resistance of a binder, and the like. Accordingly, phosphorus is frequently added to catalysts for a catalytic cracking reaction.

The catalysts for catalytic cracking that are obtained by adding phosphorus to zeolite are disclosed in, for example, Patent Documents 4 to 6.

That is, Patent Document 4 discloses a method of producing olefin from naphtha by using a catalyst containing ZSM-5 to which phosphorus, gallium, germanium, and tin has been added. Patent Document 4 aims to improve the selectivity in generating olefin by inhibiting generation of methane or an aromatic fraction by method of adding phosphorus, and to improve the yield of olefin by securing high activity with a short contact time.

Patent Document 5 discloses a method of producing olefin from heavy hydrocarbon with a high yield, by using a catalyst in which phosphorus is supported on ZSM-5 containing zirconium and a rear-earth metal and a catalyst which contains USY zeolite, REY zeolite, kaolin, silica, and alumina.

Patent Document 6 discloses a method of producing ethylene and propylene with a high yield, by converting hydrocarbon by using a catalyst containing ZSM-5 supporting phosphorus and a transition metal.

As described above, addition of phosphorus to zeolite is disclosed in Patent Documents 4 to 6. However, all of the methods mainly aimed to improve the yield of olefin, and failed to produce monocyclic aromatic hydrocarbon having 6 to 8 carbon number with a high yield. For example, Table 2 of Patent Document 6 discloses the yield of olefin (ethylene and propylene) and BTX (benzene, toluene, and xylene). In the table, while the yield of olefin is 40 mass %, the yield of BTX is as low as about 6 mass %.

Accordingly, a catalyst for producing monocyclic aromatic hydrocarbon that makes it possible to produce monocyclic aromatic hydrocarbon having 6 to 8 carbon number with a high yield from oil feedstock containing polycyclic aromatic hydrocarbon and to prevent the reduction in the yield of the monocyclic aromatic hydrocarbon over time has practically not been known.

PRIOR ART DOCUMENTS

Patent Documents

[Patent Document 1] Japanese Unexamined Patent Application, First Publication No. H3-2128
[Patent Document 2] Japanese Unexamined Patent Application, First Publication No. H3-52993
[Patent Document 3] Japanese Unexamined Patent Application, First Publication No. H3-26791
[Patent Document 4] Published Japanese Translation No. 2002-525380 of the PCT International Publication
[Patent Document 5] Japanese Unexamined Patent Application, First Publication No. 2007-190520

[Patent Document 6] Published Japanese Translation No. 2007-530266 of the PCT International Publication

DISCLOSURE OF INVENTION

Problems to be Solved by the Invention

The present invention aims to provide a catalyst for producing monocyclic aromatic hydrocarbon that makes it possible to produce monocyclic aromatic hydrocarbon having 6 to 8 carbon number with a high yield from oil feedstock containing polycyclic aromatic hydrocarbon and to prevent the reduction in the yield of the monocyclic aromatic hydrocarbon having 6 to 8 carbon number caused over time, and a production method of monocyclic aromatic hydrocarbon.

Means to Solve the Problems

[1] A catalyst for producing aromatic hydrocarbon that is for producing monocyclic aromatic hydrocarbon having 6 to 8 carbon number from oil feedstock having a 10 volume % distillation temperature of 140° C. or higher and a 90 volume % distillation temperature of 380° C. or lower, the catalyst includes crystalline aluminosilicate and phosphorus, in which a molar ratio (P/Al ratio) between phosphorus contained in the crystalline aluminosilicate and aluminum of the crystalline aluminosilicate is from 0.1 to 1.0.

[2] The catalyst for producing monocyclic aromatic hydrocarbon according to [1], in which the phosphorus content is 0.1 to 10 mass % based on the catalyst weight.

[3] The catalyst for producing monocyclic aromatic hydrocarbon according to [1] or [2], in which the crystalline aluminosilicate is medium pore size zeolite.

[4] The catalyst for producing monocyclic aromatic hydrocarbon according to any one of [1] to [3], in which the crystalline aluminosilicate is MFI-type zeolite.

[5] A production method of monocyclic aromatic hydrocarbon having 6 to 8 carbon number, including bringing oil feedstock having a 10 volume % distillation temperature of 140° C. or higher and a 90 volume % distillation temperature of 380° C. or lower into contact with the catalyst for producing monocyclic aromatic hydrocarbon according to any one of [1] to [4].

[6] The production method of monocyclic aromatic hydrocarbon having 6 to 8 carbon number according to [5], in which the oil feedstock includes light cycle oil generated from a fluidized catalytic cracking.

[7] The production method of a monocyclic aromatic hydrocarbon having 6 to 8 carbon number according to [5] or [6], further including bringing the oil feedstock into contact with the catalyst for producing monocyclic aromatic hydrocarbon by using a fluidized-bed reaction equipment.

Effect of the Invention

According to the catalyst for producing monocyclic aromatic hydrocarbon and the production method of monocyclic aromatic hydrocarbon having 6 to 8 carbon number of the present invention, monocyclic aromatic hydrocarbon having 6 to 8 carbon number may be produced with a high yield from oil feedstock containing polycyclic aromatic hydrocarbon, and the reduction in the yield of the monocyclic aromatic hydrocarbon having 6 to 8 carbon number over time may be prevented.

BEST MODE FOR CARRYING OUT THE INVENTION

Hereinafter, an embodiment of a catalyst for producing monocyclic aromatic hydrocarbon and a production method of monocyclic aromatic hydrocarbon of the present invention will be described.

(Catalyst for Producing Monocyclic Aromatic Hydrocarbon)

The catalyst for producing monocyclic aromatic hydrocarbon of the present embodiment (hereinafter, abbreviated to a "catalyst") is for producing monocyclic aromatic hydrocarbon having 6 to 8 carbon number (hereinafter, abbreviated to "monocyclic aromatic hydrocarbon") from oil feedstock containing polycyclic aromatic hydrocarbon and saturated hydrocarbon, and contains crystalline aluminosilicate and phosphorus.

[Crystalline Aluminosilicate]

The crystalline aluminosilicate is not particularly limited, but is preferably, pentasil type zeolite or medium pore size zeolite. As the medium pore size zeolite, zeolites having an MFI, MEL, TON, MTT, MRE, FER, AEL, or EUO type crystal structure are more preferable. Moreover, zeolites having an MFI and/or MEL type crystal structure are particularly preferable since they further increase the yield of monocyclic aromatic hydrocarbon.

The zeolites of MFI type, MEL type, and the like belong to zeolites having known types of structures that are publicly introduced by The Structure Commission of the International Zeolite Association (Atlas of Zeolite Structure Types, W. M. Meiyer and D. H. Olson (1978), Distributed by Polycrystal Book Service, Pittsburgh, Pa., USA).

Provided that the total amount of the catalyst (total weight of the catalyst) is 100 mass %, the content of the crystalline aluminosilicate in the catalyst is preferably 10 to 95 mass %, more preferably 20 to 80 mass %, and particularly preferably 25 to 70 mass %. When the content of the crystalline aluminosilicate is from 10 to 95 mass %, a sufficiently high degree of catalytic activity is obtained.

[Phosphorus]

A molar ratio (P/Al ratio) between phosphorus contained in the crystalline aluminosilicate and aluminum contained in the crystalline aluminosilicate is from 0.1 to 1.0. When the P/Al ratio exceeds 1.0, the yield of monocyclic aromatic hydrocarbon decreases. Accordingly, the P/Al ratio is 1.0 or lower, preferably 0.95 or lower, and more preferably 0.9 or lower.

When the P/Al ratio is lower than 0.1, the yield of monocyclic aromatic hydrocarbon in a static state decreases. Accordingly, the P/Al ratio is 0.1 or higher, preferably 0.15 or higher, and even more preferably 0.2 or higher.

Provided that the total mass of the crystalline aluminosilicate is 100 mass %, the content of phosphorus contained in the crystalline aluminosilicate in the catalyst of the present embodiment is preferably 0.1 to 3.5 mass %. Moreover, the lower limit of the content is more preferably 0.2 mass % or more, and the upper limit thereof is more preferably 3.0 mass % or less and particularly preferably 2.8 mass % or less. When the content of phosphorus supported on the crystalline aluminosilicate is 0.1 mass % or more, the reduction in the yield of monocyclic aromatic hydrocarbon caused over time can be prevented, and when it is 3.5 mass % or less, the yield of monocyclic aromatic hydrocarbon can be increased.

In addition, the upper limit of the content of phosphorus in the catalyst of the present embodiment is far lower than the upper limit of the content of phosphorus in the catalyst disclosed in Patent Documents 4 to 6. It is considered that this is because the oil feedstock of the reaction to which the catalyst of the present embodiment is applied contains a large amount of polycyclic aromatic hydrocarbon and exhibits low reactivity. In the present embodiment, when the amount of phosphorus added is too large, this makes it more difficult for the oil feedstock to react, and a degree of aromatization activity is lowered. Accordingly, the yield of monocyclic aromatic hydrocarbon is reduced. On the other hand, the oil feedstock in Patent Documents 4 to 6 (for example, vacuum gas oil or the like that is used as oil feedstock of a fluidized catalytic cracking) is heavy, has a large molecular weight, and is easily adsorbed onto a catalyst. Consequently, this oil is more easily cracked than a fraction of LCO or the like. Furthermore, because this oil is easily cracked into light olefin, a big problem does not arise even if a large amount of phosphorus is supported, and a degree of aromatization activity is lowered.

The method of adding phosphorus to the catalyst of the present embodiment is not particularly limited, and examples thereof include a method of causing phosphorus to be supported on crystalline aluminosilicate by ion exchange, impregnation, or the like, a method of replacing a portion of the inside of the crystalline aluminosilicate skeleton with phosphorus by adding a phosphorus compound during zeolite synthesis, a method of using phosphorus-containing crystallization accelerator during zeolite synthesis, or the like. An aqueous phosphate ion-containing solution used at this time is not particularly limited, and it is possible to preferably use solutions that are prepared by dissolving phosphoric acid, diammonium hydrogen phosphate, ammonium dihydrogen phosphate, other water-soluble phosphoric acid salts, or the like in water at any concentration.

The catalyst of the present embodiment is obtained by baking (baking temperature of 300 to 900° C.) the above phosphorus-containing crystalline aluminosilicate.

[Shape]

The catalyst of the present embodiment is shaped into, for example, powder, granules, pellets, or the like, according to the reaction mode.

For example, the catalyst is shaped into powder in the case of a fluidized bed and shaped into granules or pellets in the case of a fixed bed. An average particle size of the catalyst used in a fluidized bed is preferably 30 to 180 and more preferably 50 to 100 μm. Moreover, a bulk density of the catalyst used in a fluidized bed is preferably 0.4 to 1.8 g/cc, and more preferably 0.5 to 1.0 g/cc.

The average particle size indicates a size of particles accounting for 50 mass % in a particle size distribution obtained by classification performed by sieving, and the bulk density is a value measured by the method of JIS standard R9301-2-3.

In order to obtain a catalyst having a granule or pellet shape, an inactive oxide as a binder or the like may be optionally mixed in crystalline aluminosilicate or a catalyst, and then the resultant may be molded using various molding machines. Examples of the inactive oxide include silica, alumina, zirconia, titania, a mixture of these, or the like.

When the catalyst of the present embodiment contains an inorganic oxide such as a binder, those containing phosphorus as a binder may be used. Examples of the inorganic oxide such as a binder include silica, alumina, zirconia, titania, a mixture of these, and the like. When the catalyst contains the inorganic oxide such as a binder, the amount of binder is preferably 10 to 80 mass %, and more preferably 25 to 75 mass %, based on the total weight of the catalyst.

Moreover, when the catalyst contains an inorganic catalyst such as a binder, the catalyst may be produced by mixing the binder or the like with crystalline aluminosilicate and then adding phosphorus thereto.

When the catalyst contains the inorganic oxide such as a binder, the content of phosphorus is preferably 0.1 to 10 mass %, based on the total weight of the catalyst. In addition, the lower limit of the content is preferably 0.5 mass % or more, and the upper limit thereof is preferably 9 mass % or less and particularly preferably 8 mass % or less. When the content of phosphorus based on the total weight of the catalyst is 0.1 mass % or more, the reduction in the yield of monocyclic aromatic hydrocarbon caused over time can be prevented, and when it is 10 mass % or less, the yield of monocyclic aromatic hydrocarbon can be increased.

(Production Method of Monocyclic Aromatic Hydrocarbon)

The production method of monocyclic aromatic hydrocarbon of the present embodiment is a method of bringing oil feedstock into contact with the catalyst to cause a reaction.

The reaction is a method in which the oil feedstock is caused to come into contact with an acid point of the catalyst to cause various reactions such as cracking, dehydrogenation, cyclization, and hydrogen transfer, whereby polycyclic aromatic hydrocarbon undergoes ring opening and is converted into monocyclic aromatic hydrocarbon.

[Oil Feedstock]

The oil feedstock used in the present embodiment is oil having a 10 volume % distillation temperature of 140° C. or higher and a 90 volume % distillation temperature of 380° C. or lower. When oil having a 10 volume % distillation temperature of lower than 140° C. is used, BTX is produced from light oil, and this does not fit for the main object of the present embodiment. Accordingly, the 10 volume % distillation temperature of the oil is preferably 140° C. or higher, and more preferably 150° C. or higher. Moreover, when oil feedstock having a 90 volume % distillation temperature of higher than 380° C. is used, the amount of coke deposited onto the catalyst increases, whereby the catalytic activity tends to be rapidly reduced. Accordingly, the 90 volume % distillation temperature of the oil feedstock is preferably 380° C. or lower, and more preferably 360° C. or lower. In addition, the 10 volume % distillation temperature, 90 volume % distillation temperature, and endpoint described herein are values measured based on JIS K2254 "Petroleum products-Determination of distillation characteristics".

Examples of the oil feedstock having a 10 volume % distillation temperature of 140° C. or higher and a 90 volume % distillation temperature of 380° C. or lower include Light Cycle Oil (LCO) generated by a fluidized catalytic cracking, coal-liquefied oil, hydrocracked and refined heavy oil, straight-run kerosene, straight-run light oil, coker kerosene, coker light oil, hydrocracked and refined sand oil, and the like. Among these, Light Cycle Oil (LCO) generated by a fluidized catalytic cracking is preferably included in the oil feedstock.

When the oil feedstock contains a large amount of polycyclic aromatic hydrocarbon, the yield of monocyclic aromatic hydrocarbon having 6 to 8 carbon number decreases. Accordingly, the content of polycyclic aromatic hydrocarbon (polycyclic aromatic fraction) in the oil feedstock is preferably 50 volume % or less, and more preferably 30 volume % or less.

In addition, the polycyclic aromatic fraction described herein refers to the sum of the content of bicyclic aromatic hydrocarbon (bicyclic aromatic fraction) and the content of aromatic hydrocarbon having three or more rings (aromatic fraction having three or more rings) that are measured based on JPI-5S-49 "Petroleum products-Determination of hydrocarbon types-High performance liquid chromatography".

[Reaction Mode]

As the reaction mode at the time when the oil feedstock is brought into contact with the catalyst and reacted, a fixed bed, a moving bed, a fluidized bed, or the like can be used. In the present embodiment, a heavy fraction is used as oil feedstock. Accordingly, a fluidized bed that makes it possible to continuously remove the coke component attached to the catalyst and to stably carry out the reaction is preferable. Particularly, a continuously regenerative type fluidized bed in which a catalyst is circulated between a reactor and a regenerator so that reaction-regeneration can be continuously repeated, is particularly preferred. It is preferable that the oil feedstock to be brought into contact with the catalyst be in a gaseous state.

Moreover, the oil feedstock may be optionally diluted with gas, and when unreacted oil is generated, this may be optionally recycled.

[Reaction Temperature]

The reaction temperature at the time when the oil feedstock is brought into contact with the catalyst and reacted is not particularly limited, but is preferably 350 to 700° C. The lower limit of the temperature is more preferably 450° C. or higher since sufficient reaction activity is obtained. On the other hand, the upper limit thereof is more preferably 650° C. or lower since this temperature is advantageous in view of energy and makes it possible to easily regenerate the catalyst.

[Reaction Pressure]

The reaction pressure at the time when the oil feedstock is brought into contact with the catalyst and reacted is preferably 1.5 MPaG or lower, and more preferably 1.0 MPaG or lower. When the reaction pressure is 1.5 MPaG or lower, it is possible to prevent light gas from being additionally generated and to diminish pressure resistance of the reaction device. Though not particularly limited, the lower limit of the reaction pressure is preferably equal to or higher than normal pressure in view of cost and the like.

[Contact Time]

The time for which the oil feedstock comes into contact with the catalyst is not particularly limited as long as a substantially desired reaction is caused. For example, the contact time is preferably 1 to 300 sec in terms of the time required for gas on the catalyst to pass. The lower limit of the contact time is more preferably 5 sec or longer, and the upper limit thereof is more preferably 150 sec or shorter. When the contact time is 1 sec or longer, the reaction can be caused reliably, and when it is 300 sec or shorter, it is possible to inhibit a carbonaceous substance from being accumulated onto the catalyst by coking or the like and to suppress the amount of light gas generated by cracking.

In the production method of monocyclic aromatic hydrocarbon of the present embodiment, the oil feedstock is brought into contact with an acid point of the catalyst to cause various reactions such as cracking, dehydrogenation, cyclization, and hydrogen transfer and cause ring opening of polycyclic aromatic hydrocarbon, thereby obtaining monocyclic aromatic hydrocarbon.

In the present embodiment, the yield of monocyclic aromatic hydrocarbon is preferably 15 mass % or more, more preferably 20 mass % or more, and even more preferably 25 mass % or more. If the yield of monocyclic aromatic hydrocarbon is less than 15 mass %, this is not preferable since the concentration of the target substance in the product decreases, and collecting efficiency is lowered.

The production method of the present embodiment described above uses the catalyst described above. Accordingly, with this method, it is possible to produce monocyclic aromatic hydrocarbon with a high yield and to prevent the reduction in the yield of monocyclic aromatic hydrocarbon caused over time.

EXAMPLE

Hereinafter, the present invention will be described in more detail based on examples and comparative examples, but the present invention is not limited to these examples.

Example 1

A solution (A) containing 1706.1 g of sodium silicate (J sodium silicate No. 3, $SiO_2$: 28 to 30 mass %, Na: 9 to 10 mass %, balance: water, manufactured by Nippon chemical industrial Co., LTD.) and 2227.5 g of water and a solution (B) containing 64.2 g of $Al_2(SO_4)_3 \cdot 14$ to $18H_2O$ (special grade chemical, manufactured by Wako Pure Chemical Industries, Ltd.), 369.2 g of tetrapropylammonium bromide, 152.1 g of $H_2SO_4$ (97 mass %), 326.6 g of NaCl, and 2975.7 g of water were prepared respectively.

Subsequently, while the solution (A) was being stirred at room temperature, the solution (B) was slowly added to the solution (A).

The obtained mixture was vigorously stirred with a mixer for 15 minutes to crack the gel, whereby the mixture was put in the state of a homogenous fine emulsion.

Thereafter, the mixture was put in a stainless steel autoclave and subjected to crystallization operation under a self-pressure in natural course of events, a temperature of 160° C. and a stirring speed of 100 rpm for 72 hours. After the crystallization operation ended, the product was filtered to collect a solid product, and the operation in which the solid product was washed with about 5 L of deionized water and filtered was repeated 5 times. The solid content separated and obtained by filtration was dried at 120° C. and baked for 3 hours at 550° C. under an air flow.

X-ray diffraction analysis (name of instrument: Rigaku RINT-2500V) was performed on the obtained baked product, and as a result, it was confirmed that the product has an MFI structure. Moreover, a $SiO_2/Al_2O_3$ ratio (molar ratio) confirmed by X-ray fluorescence analysis (name of instrument: Rigaku ZSX101e) was 64.8. In addition, the content of aluminum element contained in the lattice skeleton that was calculated from the above result was 1.32 mass %.

A 30 mass % aqueous ammonium nitrate solution was added to the obtained baked product in such a ratio that 5 mL of the solution was added to 1 g of the product. The mixture was heated for 2 hours at 100° C. and stirred, followed by filtration and washing with water. This operation was repeated 4 times, and then the resultant was dried for 3 hours at 120° C., thereby obtaining ammonium-type crystalline aluminosilicate. Thereafter, baking was performed for 3 hours at 780° C., thereby obtaining proton-type crystalline aluminosilicate.

Subsequently, the obtained proton-type crystalline aluminosilicate is impregnated with 30 g of an aqueous diammonium hydrogen phosphate solution such that 0.2 mass % (value calculated when the total weight of the catalyst is regarded as being 100 mass %) of phosphorus was contained in 30 g of the proton-type crystalline aluminosilicate, followed by drying at 120° C. Thereafter, the resultant was baked for 3 hours at 780° C. under an air flow, thereby obtaining a catalyst containing crystalline aluminosilicate and phosphorus.

In the obtained catalyst, a molar ratio (P/Al ratio) between phosphorus contained in the crystalline aluminosilicate and aluminum of the crystalline aluminosilicate was 0.14, and the content of phosphorus based on the total weight of the catalyst was 0.2 mass %.

A pressure of 39.2 MPa (400 kgf) was applied to the obtained catalyst to form tablets, and the resultant was coarsely pulverized to have a size of 20 to 28 mesh, thereby obtaining a granular catalyst 1 (hereinafter, called a "granulated catalyst 1").

Example 2

A granular catalyst 2 (hereinafter, called a "granulated catalyst 2") was obtained in the same manner as in Example 1, except that the concentration of an aqueous diammonium hydrogen phosphate solution was adjusted such that 0.7 mass % (value calculated when the total weight of the catalyst is regarded as being 100 mass %) of phosphorus was contained in 30 g of proton-type crystalline aluminosilicate, and the proton-type crystalline aluminosilicate was impregnated with 30 g of the aqueous solution.

In the obtained catalyst, a molar ratio (P/Al ratio) between phosphorus contained in crystalline aluminosilicate and aluminum of crystalline aluminosilicate was 0.50, and the content of phosphorus based on the total weight of the catalyst was 0.7 mass %.

Example 3

A granular catalyst 3 (hereinafter, called a "granulated catalyst 3") was obtained in the same manner as in Example 1, except that the concentration of an aqueous phosphoric acid solution was adjusted such that 1.2 mass % (value calculated when the total weight of the catalyst is regarded as being 100 mass %) of phosphorus is added to 30 g of proton-type crystalline aluminosilicate, and the proton-type crystalline aluminosilicate is impregnated with 30 g of the aqueous solution.

In the obtained catalyst, a molar ratio (P/Al ratio) between phosphorus contained in the crystalline aluminosilicate and aluminum of the crystalline aluminosilicate was 0.86, and the content of phosphorus based on the total weight of the catalyst was 1.2 mass %.

Example 4

Fumed silica was impregnated with 30 g of an aqueous diammonium hydrogen phosphate solution such that 16.2 mass % of phosphorus was contained in 18 g of the fumed silica, followed by drying at 120° C. Thereafter, the resultant was baked for 3 hours at 780° C. under an air flow, thereby obtaining phosphorus-containing fumed silica. 18 g of the phosphorus-containing fumed silica was mixed with 12 g of the catalyst 2 prepared in Example 2, and a pressure of 39.2 MPa (400 Kgf) was applied to the obtained catalyst to form tablets. The resultant was coarsely pulverized to have a size of 20 to 28 mesh, thereby obtaining a granular catalyst 4 (hereinafter, called a "granulated catalyst 4").

In the obtained catalyst, a molar ratio (P/Al ratio) between phosphorus contained in the crystalline aluminosilicate and aluminum of the crystalline aluminosilicate was 0.50, and the content of phosphorus based on the total weight of the catalyst was 10 mass %.

Example 5

A mixed solution containing 106 g of sodium silicate (J sodium silicate No. 3, $SiO_2$: 28 to 30 mass %, Na: 9 to 10 mass %, balance: water, manufactured by Nippon chemical industrial Co., LTD.) and pure water was added dropwise to diluted sulfuric acid, thereby preparing an aqueous silica sol solution ($SiO_2$ concentration of 10.2%). In addition, distilled water was added to 20.4 g of the catalyst 2 that was prepared in Example 2 and contained crystalline aluminosilicate and phosphorus, thereby preparing zeolite slurry. The zeolite slurry was mixed with 300 g of the aqueous silica sol solution, and the thus prepared slurry was spray-dried at 250° C., thereby obtaining a spherical catalyst. Thereafter, the catalyst was baked for 3 hours at 600° C., thereby obtaining a catalyst 5 having a powder shape (hereinafter, called a "powdery catalyst 5") that had an average particle size of 84 pun and a bulk density of 0.74 g/cc.

In the obtained catalyst, a molar ratio (P/Al ratio) between phosphorus contained in the crystalline aluminosilicate and aluminum of the crystalline aluminosilicate was 0.50, and the content of phosphorus based on the total weight of the catalyst was 0.28 mass %.

Comparative Example 1

A granular catalyst 6 (hereinafter, called a "granulated catalyst 6") was obtained in the same manner as in Example 1, except that the concentration of an aqueous diammonium hydrogen phosphate solution was adjusted such that 2.0 mass % (value calculated when the total weight of the catalyst is regarded as being 100 mass %) of phosphorus was contained in 30 g of proton-type crystalline aluminosilicate, and the crystalline aluminosilicate was impregnated with 30 g of the aqueous solution.

In the obtained catalyst, a molar ratio (P/Al ratio) between phosphorus contained in the crystalline aluminosilicate and aluminum of the crystalline aluminosilicate was 1.43, and the content of phosphorus based on the total weight of the catalyst was 2.0 mass %.

Comparative Example 2

A granular catalyst 7 (hereinafter, called a "granulated catalyst 7") was obtained in the same manner as in Example 1, except that proton-type crystalline aluminosilicate was used as it was.

The catalytic activity of the obtained granulated catalyst at the initial stage of reaction and after hydrothermal deterioration was evaluated as below.

[Evaluation of Catalytic Activity at the Initial Stage of Reaction: Evaluation 1]

By using a circulation-type reaction device including a reactor filled with the granulated catalysts 1 to 4, 6, and 7 (10 ml) respectively, the oil feedstock having properties shown in Table 1 was brought into contact with the granulated catalyst and reacted, at a reaction temperature of 550° C. and a reaction pressure of 0 MPaG. At this time, nitrogen as a diluent was introduced into the device such that oil feedstock came into contact with the granulated catalyst for 7 seconds.

The reaction was caused for 30 minutes under the above conditions, thereby producing monocyclic aromatic hydrocarbon having 6 to 8 carbon number. By using an FID gas chromatograph directly connected to the reaction device, the composition of the product was analyzed to evaluate the catalytic activity at the initial stage of the reaction. The evaluation results are shown in Table 2A to 2C.

In Table 2A to 2C a heavy fraction in the product refers to hydrocarbon that is not included in monocyclic aromatic hydrocarbon having 6 to 8 carbon number and has 6 or more carbon number, light naphtha refers to hydrocarbon having 5 to 6 carbon number, liquefied petroleum gas refers to hydrocarbon having 3 to 4 carbon number, and cracked gas refers to hydrocarbon having 2 or less carbon number.

[Evaluation of Catalytic Activity after Hydrothermal Deterioration: Evaluation 2]

Each of the granulated catalysts 1 to 4 and 7 was subjected to hydrothermal treatment at a treatment temperature of 650° C. for a treatment time of 6 hours in an environment of 100 mass % of water vapor, thereby preparing pseudo-deteriorated catalysts 1 to 4 and 7 that were caused to undergo pseudo-hydrothermal deterioration.

The oil feedstock was reacted in the same manner as in Evaluation 1, except that the pseudo-deteriorated catalysts 1 to 4 and 7 were used respectively instead of the granulated catalysts 1 to 4 and 7. The composition of the thus obtained products was analyzed to evaluate the catalytic activity after hydrothermal deterioration. The evaluation results are shown in Table 2A to 2C.

[Evaluation of Yield of Monocyclic Aromatic Hydrocarbon at the Initial Stage of Reaction: Evaluation 3]

By using a circulation-type reaction device including a reactor filled with the powdery catalyst 5 (400 g), the oil feedstock having properties shown in Table 1 was brought into contact with the powdery catalyst 5 and reacted, at a reaction temperature of 550° C. and a reaction pressure of 0.1 MPaG. At this time, the powdery catalyst was filled in a reaction tube having a diameter of 60 mm. As a diluent, nitrogen was introduced into the device such that the oil feedstock came into contact with the powdery catalyst for 10 seconds.

The reaction was caused for 10 minutes under the above condition, thereby producing monocyclic aromatic hydrocarbon having 6 to 8 carbon number. By using an FID gas chromatograph directly connected to the reaction device, the composition of the product was analyzed to evaluate the catalytic activity at the initial stage of the reaction. The evaluation results are shown in Table 2B.

In Table 2B, a heavy fraction in the product refers to hydrocarbon that is not included in monocyclic aromatic hydrocarbon having 6 to 8 carbon number and has 6 or more carbon number, light naphtha refers to hydrocarbon having 5 to 6 carbon number, liquefied petroleum gas refers to hydrocarbon having 3 to 4 carbon number, and cracked gas refers to hydrocarbon having 2 or less carbon number.

[Evaluation of Catalytic Activity After Hydrothermal Deterioration: Evaluation 4]

The powdery catalyst 5 was subjected to hydrothermal treatment at a treatment temperature of 650° C. for a treatment time of 6 hours in an environment of 100 mass % of water vapor, thereby preparing pseudo-deteriorated catalyst 5 that was caused to undergo pseudo-hydrothermal deterioration.

The oil feedstock was reacted in the same manner as in Evaluation 3, except that the pseudo-deteriorated catalyst 5 was used instead of the powdery catalyst 5. The composition of the thus obtained product was analyzed to evaluate the catalytic activity after hydrothermal deterioration. The evaluation results are shown in Table 2B.

[Catalyst Deterioration]

A value of the amount (mass %) of monocyclic aromatic hydrocarbon having 6 to 8 carbon number in the evaluation (Evaluation 2 or 4) of catalytic activity after hydrothermal deterioration with respect to a value of the amount (mass %) of monocyclic aromatic hydrocarbon having 6 to 8 carbon number in the evaluation (Evaluation 1 or 3) of catalytic activity at the initial stage of the reaction ([amount (mass %) of monocyclic aromatic hydrocarbon having 6 to 8 carbon number in Evaluation 2 (or 4)]/[amount (mass %) of monocyclic aromatic hydrocarbon having 6 to 8 carbon number in Evaluation 1 (or 3)]) was calculated to determine the degree of catalyst deterioration. The results are also shown in Table 2A to 2C. The larger value means that the catalyst hard to deteriorate. In addition, the amount of monocyclic aromatic hydrocarbon having 6 to 8 carbon number will be abbreviated to the amount of monocyclic aromatic hydrocarbon in some cases.

TABLE 1

| Properties of raw material | | | | Method of analysis |
|---|---|---|---|---|
| Density (measured at 15° C.) | | g/cm$^3$ | 0.908 | JIS K 2249 |
| Kinetic viscosity (measured at 30° C.) | | mm$^2$/s | 3.645 | JIS K 2283 |
| Distillation properties | Initial boiling point | ° C. | 177.5 | JIS K 2254 |
| | 10 volume % distillation temperature | ° C. | 226.5 | |
| | 50 volume % distillation temperature | ° C. | 276.0 | |
| | 90 volume % distillation temperature | ° C. | 350.0 | |
| | Final point | ° C. | 377.0 | |
| Composition analysis | Saturated fraction | volume % | 34 | JPI-5S-49 |
| | Olefin fraction | volume % | 8 | |
| | Total aromatic fraction | volume % | 58 | |
| | Monocyclic aromatic fraction | volume % | 23 | |
| | Bicyclic aromatic fraction | volume % | 26 | |
| | Aromatic fraction having 3 or more rings | volume % | 9 | |

TABLE 2A

| Method of preparing granular catalyst | Example 1 | Example 2 | Example 3 |
|---|---|---|---|
| Phosphorus contained in crystalline aluminosilicate/aluminum of crystalline aluminosilicate (P/Al ratio) (molar ratio) | 0.14 | 0.5 | 0.86 |

TABLE 2A-continued

|  |  | Evaluation 1 | Evaluation 2 | Evaluation 1 | Evaluation 2 | Evaluation 1 | Evaluation 2 |
| --- | --- | --- | --- | --- | --- | --- | --- |
| Content of phosphorus based on weight of catalyst (mass %) | | 0.2 | | 0.7 | | 1.2 | |
| Catalyst | | Granulated catalyst 1 | Pseudo-deteriorated catalyst 1 | Granulated catalyst 2 | Pseudo-deteriorated catalyst 2 | Granulated catalyst 3 | Pseudo-deteriorated catalyst 3 |
| Generated amount (mass %) | Heavy fraction | 46 | 53 | 47 | 50 | 52 | 52 |
| | Monocyclic aromatic hydrocarbon having 6 to 8 carbon number | 39 | 27 | 34 | 30 | 22 | 23 |
| | Light naphtha | 1 | 1 | 1 | 1 | 2 | 1 |
| | Liquefied petroleum gas | 4 | 9 | 8 | 8 | 14 | 13 |
| | Cracked gas | 8 | 9 | 9 | 9 | 11 | 11 |
| | Hydrogen | 1 | 1 | 1 | 1 | 0 | 0 |
| Amount (mass %) of monocyclic aromatic hydrocarbon in Evaluation 2 (or 4)/amount (mass %) of monocyclic aromatic hydrocarbon in Evaluation 1 (or 3) (mass %) | | 0.69 | | 0.9 | | 1.06 | |

TABLE 2B

| Method of preparing granular catalyst | | Example 4 | | Example 5 | |
| --- | --- | --- | --- | --- | --- |
| Phosphorus contained in crystalline aluminosilicate/aluminum of crystalline aluminosilicate (P/Al ratio) (molar ratio) | | 0.5 | | 0.5 | |
| Content of phosphorus based on weight of catalyst (mass %) | | 10 | | 0.28 | |
| | | Evaluation 1 | Evaluation 2 | Evaluation 3 | Evaluation 4 |
| Catalyst | | Granulated catalyst 4 | Pseudo-deteriorated catalyst 4 | Powdered catalyst 5 | Pseudo-deteriorated catalyst 5 |
| Generated amount (mass %) | Heavy fraction | 50 | 53 | 48 | 50 |
| | Monocyclic aromatic hydrocarbon having 6 to 8 carbon number | 23 | 22 | 31 | 28 |
| | Light naphtha | 1 | 1 | 1 | 1 |
| | Liquefied petroleum gas | 15 | 14 | 9 | 10 |
| | Cracked gas | 11 | 10 | 11 | 11 |
| | Hydrogen | 1 | 1 | 1 | 1 |

TABLE 2B-continued

| | | |
|---|---|---|
| Amount (mass %) of monocyclic aromatic hydrocarbon in Evaluation 2 (or 4)/ amount (mass %) of monocyclic aromatic hydrocarbon in Evaluation 1 (or 3) (mass %) | 0.96 | 0.9 |

TABLE 2C

| Method of preparing granular catalyst | | Comparative example 1 | Comparative example 2 |
|---|---|---|---|
| Phosphorus contained in crystalline aluminosilicate/aluminum of crystalline aluminosilicate (P/Al ratio) (molar ratio) | | 1.43 | 0.0 |
| Content of phosphorus based on weight of catalyst (mass %) | | 2.0 | 0.0 |

| | | Evaluation 1 | Evaluation 2 | Evaluation 1 | Evaluation 2 |
|---|---|---|---|---|---|
| Catalyst | | Granulated catalyst 6 | — | Granulated catalyst 7 | Pseudo-deteriorated catalyst 7 |
| Generated amount (mass %) | Heavy fraction | 58 | — | 46 | 62 |
| | Monocyclic aromatic hydrocarbon having 6 to 8 carbon number | 5 | — | 38 | 10 |
| | Light naphtha | 6 | — | 1 | 4 |
| | Liquefied petroleum gas | 21 | — | 5 | 15 |
| | Cracked gas | 10 | — | 9 | 9 |
| | Hydrogen | 0 | — | 1 | 0 |
| Amount (mass %) of monocyclic aromatic hydrocarbon in Evaluation 2 (or 4)/ amount (mass %) of monocyclic aromatic hydrocarbon in Evaluation 1 (or 3) (mass %) | | — | | 0.26 | |

[Result]

In Examples 1 to 5 using the granulated catalysts 1 to 4 and powdery catalyst 5, the amount of monocyclic aromatic hydrocarbon having 6 to 8 carbon number generated at the initial stage of the reaction was 39 mass %, 34 mass %, 22 mass %, 23 mass %, and 31 mass % respectively, and the amount of monocyclic aromatic hydrocarbon having 6 to 8 carbon number generated after hydrothermal deterioration was 27 mass %, 30 mass %, 23 mass %, 22 mass %, and 28 mass % respectively. In addition, the degree of catalyst deterioration ([amount (mass %) of monocyclic aromatic hydrocarbon in Evaluation 2 (or 4)/amount (mass %) of monocyclic aromatic hydrocarbon in Evaluation 1 (or 3)]) was 0.69, 0.90, 1.06, 0.96, and 0.90 respectively.

It was found that in Examples 1 to 5 using the granulated catalysts 1 to 4 and powdery catalyst 5, both the catalytic activity at the initial stage of the reaction and the catalytic activity after hydrothermal deterioration were excellent, and monocyclic aromatic hydrocarbon having 6 to 8 carbon was obtained with an excellent yield at the initial stage of the reaction and after hydrothermal deterioration, as the object of the present application.

On the other hand, it was found that in Comparative example 1 using the granulated catalyst 6 having a high P/Al ratio, the amount of monocyclic aromatic hydrocarbon having 6 to 8 carbon number generated at the initial stage of the reaction was 5 mass %, and when a large amount of phosphorus was added, the yield of monocyclic aromatic hydrocarbon having 6 to 8 carbon number in the product markedly decreased even at the initial stage of the reaction.

In Comparative example 2 using the granulated catalyst 7 having a P/Al ratio of 0, the amount of monocyclic aromatic hydrocarbon having 6 to 8 carbon number generated at the initial stage of the reaction was 38 mass %, the amount of monocyclic aromatic hydrocarbon having 6 to 8 carbon number generated after hydrothermal deterioration was 10 mass %, and the degree of catalyst deterioration ([amount (mass %) of monocyclic hydrocarbon in Evaluation 2/[amount (mass %) of monocyclic aromatic hydrocarbon in Evaluation 1]) was 0.26. Accordingly, it was found that when a catalyst not containing phosphorus is used, though the yield of monocyclic aromatic hydrocarbon having 6 to 8 carbon number at the initial stage of the reaction is excellent, the yield decreases after hydrothermal deterioration, and the catalyst deteriorates markedly, so the catalyst is not practical.

So far, preferable embodiments of the present invention have been described, but the present invention is not limited to the above embodiments. Within a scope that is not extrinsic to the object of the present invention, the constitutional elements can be added, omitted, substituted, and modified in another way. The present invention is restricted not by the above description but only by the claims attached.

The invention claimed is:

1. A production method of monocyclic aromatic hydrocarbon having 6 to 8 carbon number, comprising bringing oil feedstock having a 10 volume % distillation temperature of 140° C. or higher and a 90 volume % distillation temperature of 380° C. or lower into contact with a catalyst for producing monocyclic aromatic hydrocarbon, wherein the catalyst consists of a medium pore size zeolite crystalline aluminosilicate and phosphorus, wherein a molar ratio (P/Al ratio) between phosphorus contained in the crystalline aluminosilicate and aluminum of the crystalline aluminosilicate is from 0.5 to 1.0, and wherein the oil feedstock comprises at least one of light cycle oil generated by fluidized catalytic cracking, coal-liquified oil, hydrocracked and refined heavy oil, straight-run kerosene, coker kerosene, and hydrocracked and refined sand oil.

2. The production method of a monocyclic aromatic hydrocarbon having 6 to 8 carbon number according to claim 1, further comprising bringing the oil feedstock into contact with the catalyst for producing monocyclic aromatic hydrocarbon by using a fluidized-bed reaction equipment.

3. The production method of a monocyclic aromatic hydrocarbon having 6 to 8 carbon number according to claim 1, wherein the phosphorus content is 0.1 to 10 mass % based on the catalyst weight.

4. The production method of a monocyclic aromatic hydrocarbon having 6 to 8 carbon number according to claim 1, wherein the crystalline aluminosilicate is MFI-type zeolite.

5. A production method of monocyclic aromatic hydrocarbon having 6 to 8 carbon number, comprising bringing oil feedstock having a 10 volume % distillation temperature of 140° C. or higher and a 90 volume % distillation temperature of 380° C. or lower into contact with a catalyst for producing monocyclic aromatic hydrocarbon, wherein the catalyst consists of a medium pore size zeolite crystalline aluminosilicate, phosphorus, and an inactive oxide, wherein a molar ratio (P/Al ratio) between phosphorus contained in the crystalline aluminosilicate and aluminum of the crystalline aluminosilicate is from 0.5 to 1.0, and wherein the oil feedstock comprises at least one of light cycle oil generated by fluidized catalytic cracking, coal-liquified oil, hydrocracked and refined heavy oil, straight-run kerosene, coker kerosene, and hydrocracked and refined sand oil.

6. The production method of a monocyclic aromatic hydrocarbon having 6 to 8 carbon number according to claim 5, further comprising bringing the oil feedstock into contact with the catalyst for producing monocyclic aromatic hydrocarbon by using a fluidized-bed reaction equipment.

7. The production method of a monocyclic aromatic hydrocarbon having 6 to 8 carbon number according to claim 5, wherein the phosphorus content is 0.1 to 10 mass % based on the catalyst weight.

8. The production method of a monocyclic aromatic hydrocarbon having 6 to 8 carbon number according to claim 5, wherein the crystalline aluminosilicate is MFI-type zeolite.

9. The production method of a monocyclic aromatic hydrocarbon having 6 to 8 carbon number according to claim 5, wherein the inactive oxide consists of silica, alumina, zirconia, titania, and a mixture thereof.

* * * * *